(12) United States Patent
Glasmachers et al.

(10) Patent No.: US 10,393,686 B2
(45) Date of Patent: Aug. 27, 2019

(54) CONDUCTIVITY METER FOR MEASURING AN ELECTRIC CONDUCTIVITY OF A LIQUID MEDIUM

(71) Applicant: KROHNE Messtechnik GmbH, Duisburg (DE)

(72) Inventors: Holger Glasmachers, Bochum (DE); Christoph Schmits, Dortmund (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 54 days.

(21) Appl. No.: 15/720,148

(22) Filed: Sep. 29, 2017

(65) Prior Publication Data
US 2018/0088065 A1    Mar. 29, 2018

(30) Foreign Application Priority Data
Sep. 29, 2016    (DE) .................. 10 2016 118 526

(51) Int. Cl.
*G01N 27/07*    (2006.01)
*G01N 27/02*    (2006.01)

(52) U.S. Cl.
CPC ........... *G01N 27/07* (2013.01); *G01N 27/025* (2013.01)

(58) Field of Classification Search
CPC combination set(s) only.
See application file for complete search history.

(56) References Cited

U.S. PATENT DOCUMENTS

| | | | |
|---|---|---|---|
| 4,808,931 A * | 2/1989 | Ling | G01N 27/07 324/439 |
| 4,949,581 A | 8/1990 | Rud, Jr. | |
| 6,369,579 B1 | 4/2002 | Riegel | |
| 6,822,461 B2 * | 11/2004 | Klun | G01N 27/226 324/698 |
| 7,155,971 B2 | 1/2007 | Wamhof et al. | |

(Continued)

FOREIGN PATENT DOCUMENTS

| | | |
|---|---|---|
| CN | 103675349 A | 3/2014 |
| DE | 37 24 104 A1 | 2/1989 |

(Continued)

OTHER PUBLICATIONS

Conductivity Analyzer Guide, Technical Information, Yokogawa Electric Corporation, TI12D08A01-01E, 1st Edition, Jul. 2009, pp. 1-48.

*Primary Examiner* — Vinh P Nguyen
(74) *Attorney, Agent, or Firm* — David S. Safran; Roberts Mlotkowski Safran Cole & Calderon, P.C.

(57) ABSTRACT

A conductivity meter for measuring an electrical conductivity of a liquid medium having a housing, a conductive first measuring cell and a control device for controlling the first measuring cell, wherein the first measuring cell has a first conductivity measuring range, a first electrode and a second electrode, and wherein the first measuring cell and the control device are arranged at the housing. To provide a conductivity meter for measuring an electrical conductivity of a liquid medium, whose conductivity measuring range is increased, the conductivity meter has a second measuring cell with a second conductivity measuring range, that the second measuring cell is arranged at the housing, and that the control device is designed for controlling the second measuring cell.

13 Claims, 10 Drawing Sheets

(56) References Cited

U.S. PATENT DOCUMENTS

| | | | |
|---|---|---|---|
| 7,834,646 B2 * | 11/2010 | Chambon | A47J 37/1266 |
| | | | 324/686 |
| 7,837,845 B2 | 11/2010 | Abel et al. | |
| 9,347,906 B2 | 5/2016 | Gruden | |
| 9,383,284 B2 | 7/2016 | Miyashita | |
| 2017/0261588 A1 | 9/2017 | Andelic | |

FOREIGN PATENT DOCUMENTS

| | | |
|---|---|---|
| DE | 94 14 343 U1 | 11/1994 |
| DE | 10 2012 106 551 A1 | 1/2014 |
| DE | 10 2014 109 366 A1 | 1/2016 |
| WO | 2017/060307 A1 | 4/2017 |

* cited by examiner

CONDUCTIVITY METER FOR MEASURING AN ELECTRIC CONDUCTIVITY OF A LIQUID MEDIUM

BACKGROUND OF THE INVENTION

Field of the Invention

The invention relates to a conductivity meter for measuring an electrical conductivity of a liquid medium. The conductivity meter has a housing, a conductive first measuring cell and a control device for controlling the first measuring cell. The first measuring cell has a first conductivity measuring range, a first electrode and a second electrode. Thereby, the first electrode and second electrode form the first measuring cell. Further, the first measuring cell and the control device are arranged at the housing.

Description of Related Art

For many applications, an important property of liquid media is its electrical conductivity. An electrical conductivity of a liquid medium is caused by ions, wherein electrically positively charged ions are called cations and electrically negatively charged ions are called anions. The measurement of an electrical conductivity of a liquid medium is carried out, for example, with a conductive measuring cell in conjunction with a control device. For this purpose, the conductive measuring cell has a first and a second electrode which are spaced apart from one another and immersed in the liquid medium. The control device first determines the electrical conductance of the liquid medium between the first and second electrodes. The electrical conductance is proportional to the area of the first and second electrodes and is inversely proportional to the distance between the first and second electrodes. The quotient of distance and area is also referred to as the cell constant of the conductive measuring cell. The control device determines the conductance in that the control device, for example, applies a voltage between the electrodes and determines the current flowing through the voltage. The conductance is the quotient of the measured current and the applied voltage. Then, the control device determines the conductivity of the liquid medium in that the control device multiplies the conductance by the cell constant.

An electrical voltage, such as, e.g., the voltage for determining the conductance, between the first and the second electrode negatively charges the first electrode and positively charges the second electrode, whereby an electric field is produced in the liquid medium between the first and the second electrode. The electric field causes movement of the cations to the negatively charged electrode and movement of the anions to the positively charged electrode. The cations at the negatively charged electrode and the anions at the positively charged electrode create a polarization capacitance, which impairs the electric field in the medium and thus also the determination of the conductance. By means of a suitable selection of the cell constant, i.e., in suitably choosing the distance between the first and the second electrode and in appropriately choosing the area of the first and second electrodes, it is possible to reduce the impairment of the determination of the conductance by the polarization capacitance.

Conductivity meters having a conductive measuring cell are known from the prior art and have a dynamic range of approximately 100. A dynamic range of 100 means that the quotient of the maximum determinable conductivity and of the minimum determinable conductivity is 100. The maximum determinable conductivity and the minimum determinable conductivity are wherein they have the maximum measuring tolerance of the actual conductivity of a medium permissible for an application. If a conductance measured with a measuring cell is either greater than the maximum conductivity or smaller than the minimum conductivity, then the measuring tolerance is no longer tolerable for the application. However, a variety of applications require a dynamic range of well over 100.

SUMMARY OF THE INVENTION

Thus, the object of the invention is to provide a conductivity meter for measuring an electrical conductivity of a liquid medium, whose conductivity measuring range is greater in comparison to the prior art.

The above derived and described object is initially essentially achieved in that the conductivity meter has a second measuring cell with a second conductivity measuring range, that the second measuring cell is arranged at the housing, and that the control device is designed for controlling the second measuring cell. In addition to the first measuring cell with the first conductivity measuring range, the conductivity meter according to the invention accordingly also has at least one further measuring cell, namely the second measuring cell with the second conductivity measuring range, wherein the control device is designed for controlling all measuring cells.

The conductivity measuring range of the conductivity meter is determined by the first conductivity measuring range and the second conductivity measuring range. The conductivity meter according to the invention thus has the advantage over conductivity measuring devices from the prior art that the conductivity measurement range is increased.

Since the conductivity measuring range of the conductivity meter is determined by the first conductivity measuring range and the second conductivity measuring range, it is provided in a first advantageous design of the conductivity meter according to the invention that the first measuring cell and the second measuring cell are designed in such a manner that the first conductivity measuring range and the second conductivity measuring range overlap one another, so that the conductivity meter has a continuous conductivity measuring range. The conductivity measurement range, in which the first conductivity measurement range and the second conductivity measurement range overlap one another, is also referred to as overlapping conductivity measurement range. An electrical conductivity of a liquid medium which lies in the overlapping conductivity measurement range can be determined by the control device both with the first measuring cell and with the second measuring cell, whereby the determination of the electrical conductivity of the liquid medium has a redundancy.

In order to take advantage of this redundancy, it is provided in a further development of the above design that the control device is designed first for determining a first conductivity of the medium with the first measuring cell and a second conductivity of the medium with the second measuring cell. Further, the control device is designed for signaling an error if the determined first conductivity and/or the determined second conductivity lie in an overlapping conductivity measurement range and the determined first conductivity and the determined second conductivity deviate from one another by more than a conductivity tolerance value. In this case, the conductivity tolerance value of the control device is predetermined, whereby this is dependent on the particular application. This further development is based on the recognition that, in the case of a liquid medium whose electrical conductivity lies in the overlapping conductivity measurement range, both the first measuring cell and the second measuring cell must provide the same electrical conductivity within the scope of their respective measuring tolerance if no error is present. The measuring tolerance of the first measuring cell and the measuring tolerance of the second measuring cell must be taken into account when choosing the conductivity tolerance value. In particular, the conductivity tolerance value is to be selected so that it is greater than the larger of the two measurement tolerances.

In a further design, it is provided that the control device is designed to improve the reliability of safety functions by means of the redundancy due to the overlapping conductivity measuring range, whereby the safety integrity level (SIL) is increased.

In principle, on the one hand, conductive measuring cells and, on the other hand, inductive measuring cells are suitable as measuring cells for the conductivity meter. In a further design of the conductivity meter, it is provided that the second measuring cell is a conductive measuring cell. Thus, both the first measuring cell and the second measuring cell are conductive measuring cells, whereby the adaptation of the control device to the second measuring cell, so that the control device controls both the first measuring cell and the second measuring cell, is simpler than if the second measuring cell were an inductive measuring cell. In this manner, production costs are saved.

In a further development of the preceding design, it is provided for further cost savings that the conductivity meter has a third electrode and that the second electrode and the third electrode form the second measuring cell. The first and second measuring cells thus have a total of three electrodes.

In a further development of the preceding further development, in order to increase the conductivity measuring range of the conductivity meter and/or to increase the redundancy, it is provided that the first electrode and the third electrode form a third measuring cell with a third conductivity measuring range and that the control device is designed for controlling the third measuring cell. Thus, the control means not only controls the first and second measuring cells, but also the third measuring cell. Since all measuring cells are conductive measuring cells, the adaptation of the control device is simpler than if at least one of the measuring cells were an inductive measuring cell.

The spatial formation and arrangement of the measuring cells and, thus, the electrodes can take place in various manners. In one design of the formation and arrangement of the electrodes, it is provided that at least the first electrode and the second electrode are cylindrically designed and coaxially arranged one inside the other. In another design, it is provided that at least the first electrode and the second electrode are plate-shaped and arranged parallel to one another. It is provided in another design that the conductivity meter has a carrier plate and at least the first electrode and the second electrode are arranged next to one another on the carrier plate.

In a further design of the conductivity meter, it is provided that the second measuring cell is not a conductive measuring cell but an inductive measuring cell. An inductive measuring cell usually has a transmitting coil and a receiving coil. To measure an electrical conductivity of an electrically conductive liquid medium, the inductive measuring cell is immersed in the medium, whereby the transmitting coil and the receiving coil are coupled together inductively. The control device is designed to generate electrical transmitting signals and to supply them to the transmitting coil, to measure measuring signals induced in the receiving coil via the medium, and to determine the conductivity of the medium from the measuring signals.

In one design of the conductivity meter, in which the second measuring cell is an inductive measuring cell, it is provided that the conductivity meter has a cylindrical carrier and the inductive measuring cell is arranged around the cylindrical carrier. It is further provided that the first electrode and the second electrode of the first measuring cell are cylindrically designed and coaxially arranged one inside the other. Moreover, the first measuring cell and the second measuring cell are arranged coaxially one inside the other. Preferably, in the coaxial arrangement of the first measuring cell and the second measuring cell, the first measuring cell is arranged around the second measuring cell. This design is wherein the first measuring cell shields magnetic fields generated by the second measuring cell. If the inductive measuring cell has a transmitting coil and/or a receiving coil, the inductive measuring cell is arranged around the cylindrical carrier in such a manner that the transmitting coil and/or the receiving coil is or are arranged around the cylindrical carrier.

The spatial formation of the first and the second measuring cell can take place in various manners in a conductivity meter having a conductive first measuring cell and an inductive second measuring cell. In one design of the formation, it is provided that the first measuring cell is arranged next to or parallel to the second measuring cell. It is provided in a second design that the first measuring cell is arranged in series, e.g., coaxially, in front of or behind the second measuring cell. In a further design, it is provided that the first measuring cell is arranged under the second measuring cell. It is provided in a further design that the housing has a support shaft and the first measuring cell is arranged in or on the support shaft.

It is provided in a further design of the conductivity meter that the control device has a changeover switch, that the changeover switch is controlled by the control device, and that the changeover switch connects the control device at least to the first measuring cell or the second measuring cell. The changeover switch allows the use of a single control device for the at least first and second measuring cell. When the changeover switch connects the control device to one of the measuring cells for controlling this measuring cell using the control device, this is an exclusive connection, which means that only this measuring cell is controlled by the control device.

In detail, there is a plurality of possibilities for designing and further developing the conductivity meter according to the invention as will be apparent from the following description of preferred embodiments in conjunction with the accompanying drawings.

DETAILED DESCRIPTION OF THE INVENTION

Figure 1:
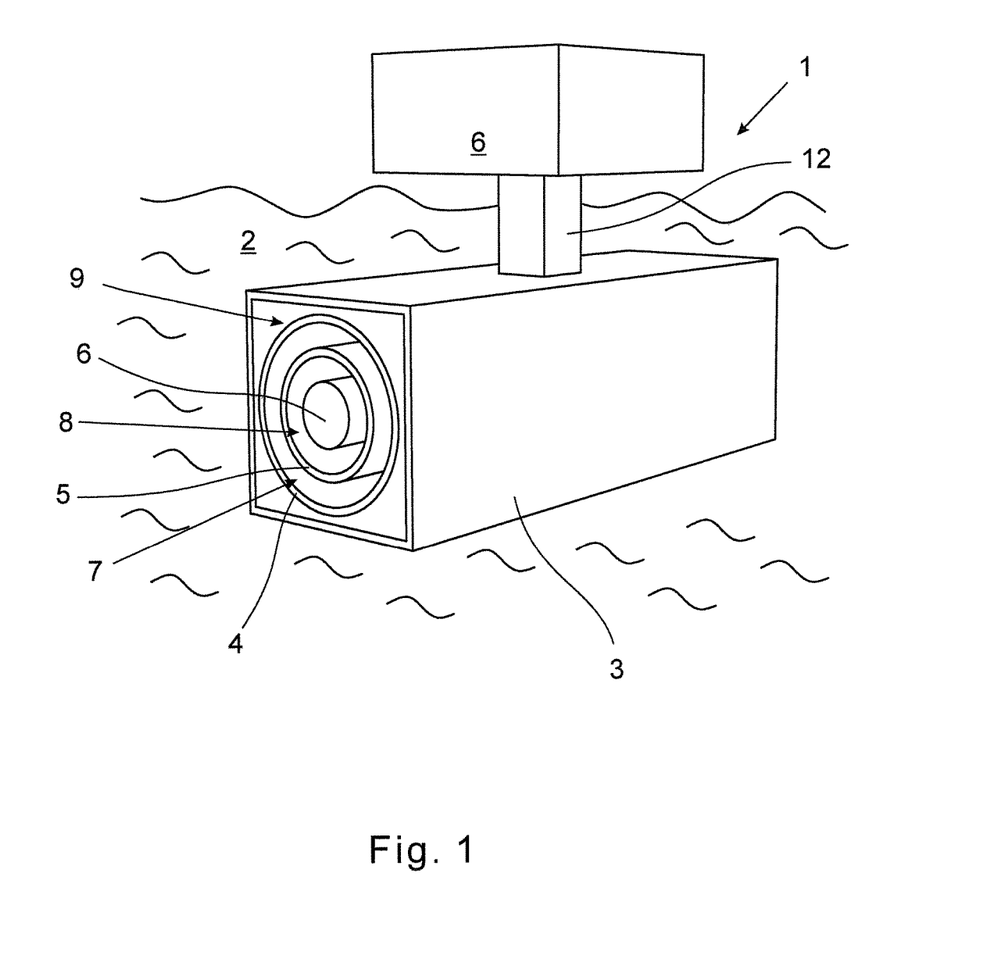
FIG. 1 is a perspective view of a first embodiment of a conductivity meter having a first and second conductive measuring cell in one arrangement.
Figure 2:
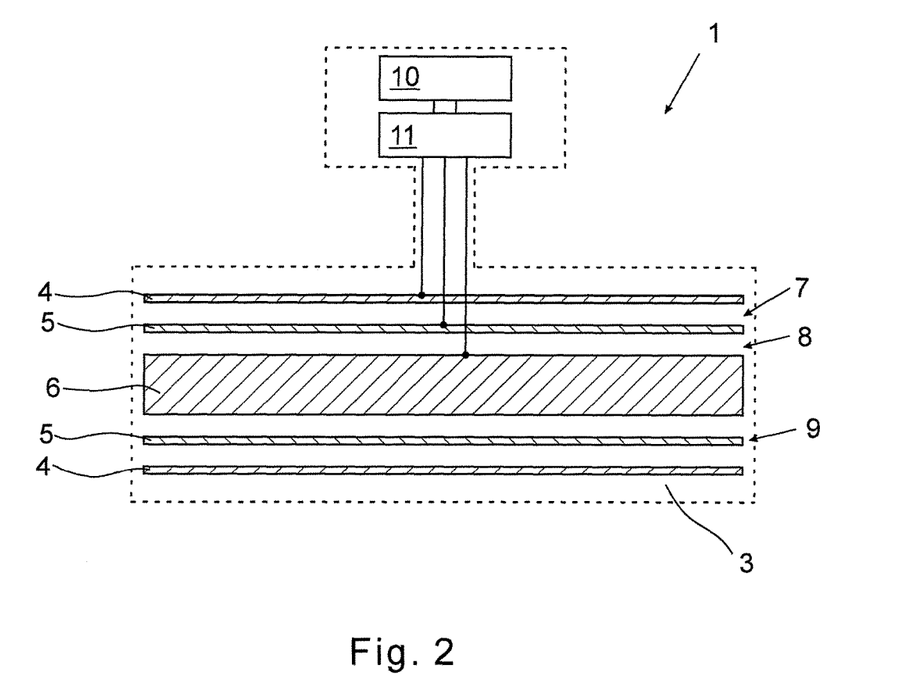
FIG. 2 is a sectional view of the conductivity meter from FIG. 1, FIG. 3 diagrammatically shows a second embodiment of a conductivity meter having a conductive first and second measuring cell in a further arrangement, FIG. 4 diagrammatically shows a third embodiment of a conductivity meter having conductive first and second measuring cell in another arrangement.

FIG. 1 shows a first embodiment of a conductivity meter 1 for the measurement of an electrical conductivity of a liquid medium 2 in an abstracted representation. FIG. 2 shows the embodiment in a sectional view. The conductivity meter 1 has a housing 3, a first electrode 4, a second electrode 5 and a third electrode 6, wherein the electrodes 4, 5, 6 are arranged at the housing 3. The first electrode 4 and the second electrode 5 form a conductive first measuring cell 7 with a first conductivity measuring range, the second electrode 5 and the third electrode 6 form a conductive second measuring cell 8 with a second conductivity measuring range and the first electrode 4 and the third electrode 6 form a conductive third measuring cell 9 with a third conductivity measuring range. In particular, on the one hand, the medium 2 is between the first electrode 4 and the second electrode 5, and on the other hand, between the second electrode 5 and the third electrode 6 and in contact with the electrodes 4, 5, 6. Due to the arrangement of the electrodes 4, 5, 6 at the housing 3, the measuring cells 7, 8, 9 are also arranged at the housing. Each of the measuring cells 7, 8, 9 has a cell constant, wherein the cell constants are determined in such a way that, on the one hand, the first conductivity measuring range and the second conductivity measuring range overlap one another so that a first overlapping conductivity measurement range arises, and on the other hand, that the second conductivity measuring range and the third conductivity measuring range overlap one another, so that a second overlapping conductivity measuring range is formed.

In addition, the conductivity meter 1 has a control device 10 with a change-over switch 11, wherein the control device 10 is designed for controlling the change-over switch 11. In addition, the control device 10 is also designed for controlling the measuring cells 7, 8, 9. The changeover switch 11 allows the use of the single control device 10 with the plurality of measuring cells 7, 8, 9. The changeover switch 11, controlled by the control device 10, connects the control device 10 either with the first measuring cell 7 or the second measuring cell 8 or the third measuring cell 9, so that, during operation, the control device 10 determines a conductivity of the liquid medium 2 at one point in time with one of the measuring cells 7, 8, 9, respectively. In this case, the connection between the control device 10 and one of the measuring cells 7, 8, 9 is exclusive, which means that the other two measuring cells cannot then be controlled by the control device 10. The design of the control device 10 for controlling the measuring cells 7, 8, 9 comprises, in particular, the configuration for determining a conductivity of a medium with the measuring cells 7, 8, 9.

Furthermore, the control device 10 is designed to first determine, during operation, a first conductivity of the medium 2 with the first measuring cell 7 and a second conductivity of the medium 2 with the second measuring cell 8, and then, to signal an error if the determined first conductivity and/or the determined second conductivity lie or lies in the first overlapping conductivity measurement range and the determined first conductivity and the determined second conductivity differ by more than a conductivity tolerance value stored in the control device 10. Correspondingly, the control device 10 is designed to first determine a first conductivity of the medium 2 with the second measuring cell 8 and a second conductivity of the medium 2 with the third measuring cell 9 and then to signal an error if the determined first conductivity and/or second conductivity lie or lies in the second overlapping conductivity measurement range and the determined first conductivity and the determined second conductivity deviate from one another by more than the conductivity tolerance value. This embodiment of the control device 10 is based on the recognition that, in the case of a liquid medium whose electrical conductivity lies either in the first overlapping conductivity measuring range or in the second overlapping conductivity measuring range, either the first measuring cell 7 and the second measuring cell 8 or the second measuring cell 8 and the third measuring cell 9 in the scope of their respective measurement tolerances would have to provide the same electrical conductivity of the medium 2 if there was no error. When selecting the conductivity tolerance value, the measuring tolerances of the measuring cells 7, 8, 9 must be taken into account. In particular, the conductivity tolerance value is to be selected to be greater than the largest of the three measurement tolerances.

The housing 3 of the conductivity meter 1 also has a support shaft 12 to which the conductivity meter 1 can be attached, so that the measuring cells 7, 8, 9 are immersed in the conductive liquid medium 2. In addition, the support shaft 12 connects the part of the housing 3, in which the control device 10 and the changeover switch 11 are arranged, to the part of the housing 3 in which the measuring cells 7, 8, 9 are arranged. Electrical connection lines, which connect the electrodes 4, 5, 6 to the changeover switch 11, usually also extend in the holding shaft 12.

In this embodiment, the electrodes 4, 5, 6 are cylindrical in shape. The first electrode 4 and the second electrode 5 are, in each case, a hollow cylinder, and the third electrode 6 is a solid cylinder made of an electrically conductive material. The electrodes 4, 5, 6 are coaxially arranged one inside the other.

Figure 3:
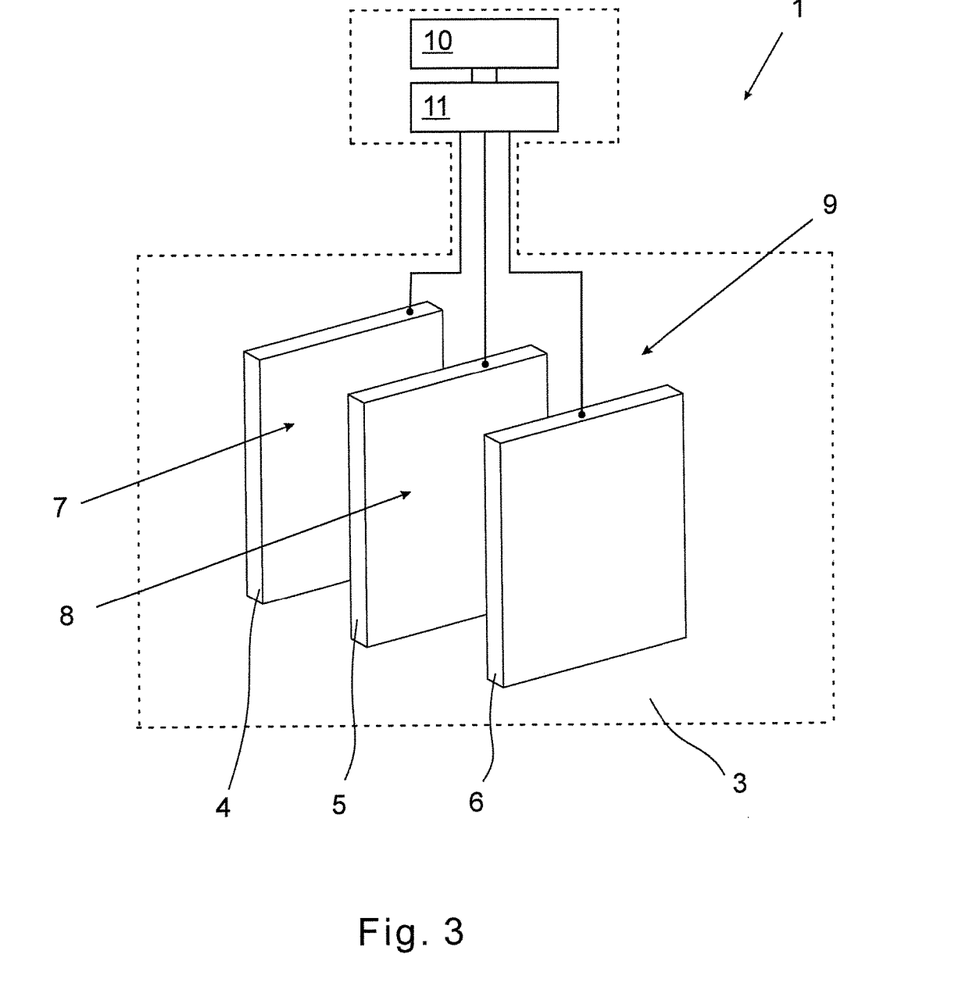

FIG. 3 shows a second embodiment of a conductivity meter 1 in an abstracted sectional view. This embodiment corresponds to the first embodiment apart from the differences indicated in the following, which is why the comments in respect to the first embodiment correspondingly apply to the second embodiment.

As in the first embodiment, the second embodiment of the conductivity meter 1 has a first electrode 4, a second electrode 5 and a third electrode 6, wherein the electrodes are not cylindrical but plate-shaped. The electrodes are also not arranged coaxially in one another, but parallel to one another.

Figure 4:
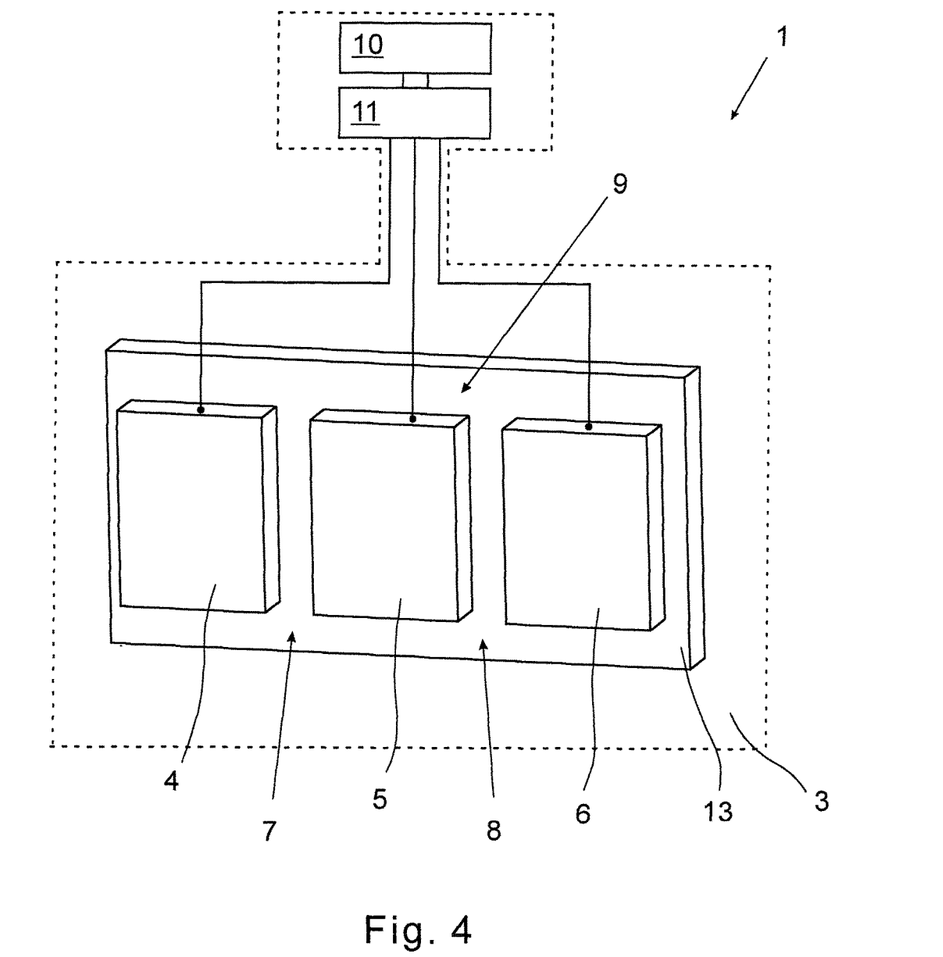

FIG. 4 shows a third embodiment of a conductivity meter 1 in an abstracted sectional view. This embodiment corresponds to the first embodiment apart from the differences shown in the following, which is why the comments in respect to the first embodiment correspondingly apply to the third embodiment.

The third embodiment of the conductivity meter 1, like the first embodiment, has a first electrode 4, a second electrode 5 and a third electrode 6. In addition, the conductivity meter 1 has a carrier plate 13, on which the first electrode 4, the second electrode 5 and the third electrode 6 are arranged next to one another.

Figure 5:
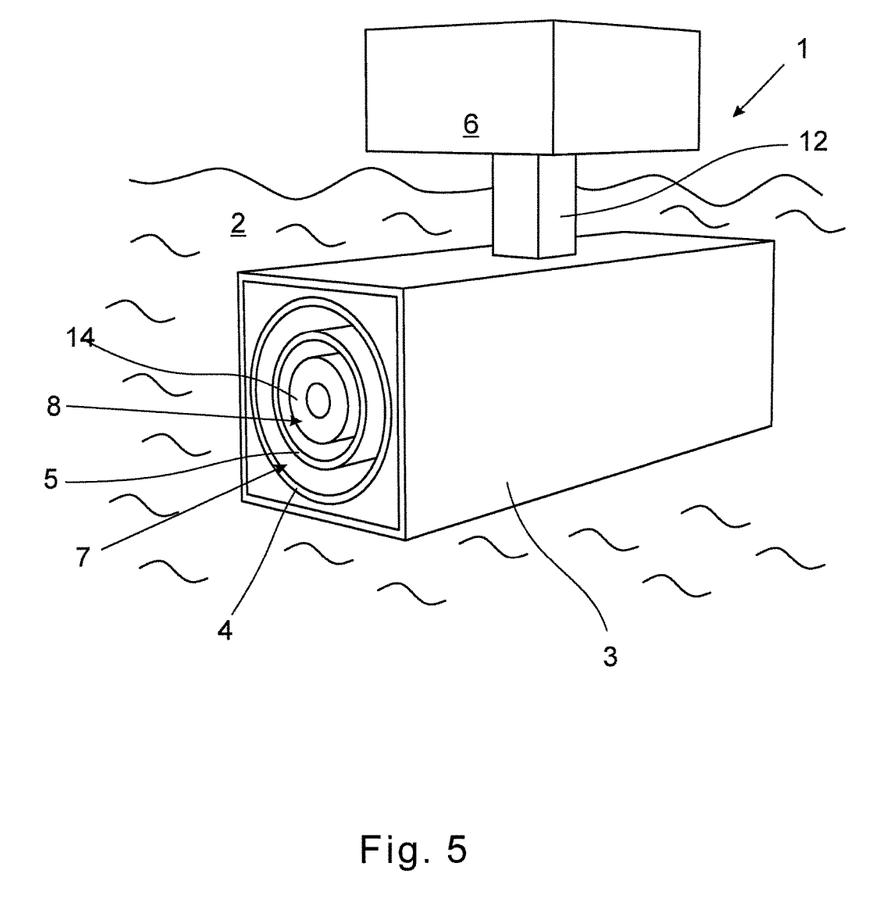
FIG. 5 is a perspective view of a fourth embodiment of a conductivity meter having a conductive first measuring cell and an inductive second measuring cell.
Figure 6:
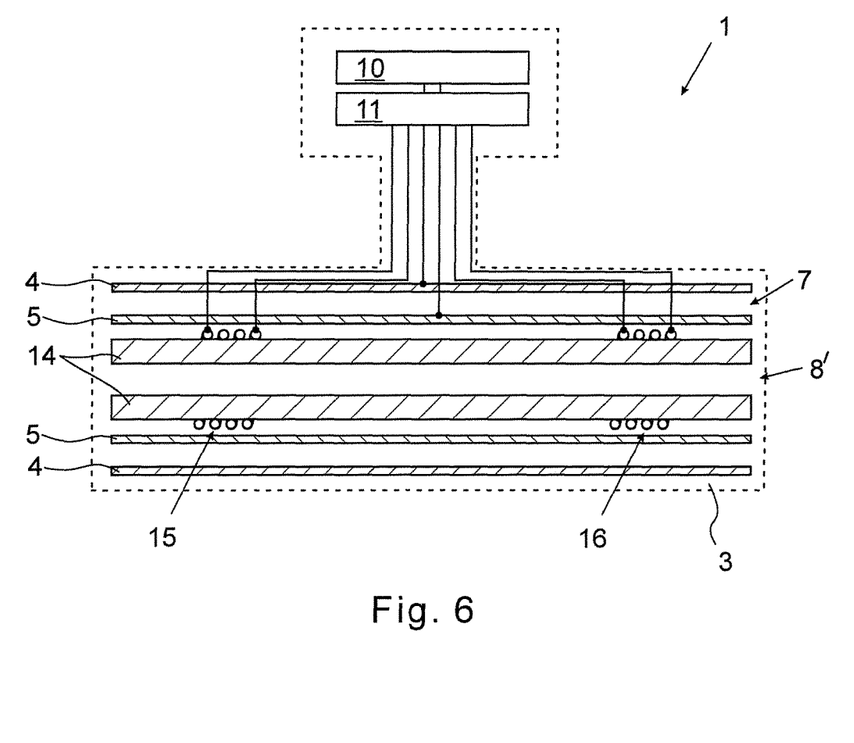
FIG. 6 is a diagrammatic view of the conductivity meter from FIG. 5.

FIG. 5 shows, in an abstracted representation, a fourth embodiment of a conductivity meter 1 for measuring an electrical conductivity of a liquid medium 2 having a housing 3, a conductive first measuring cell 7 and an inductive second measuring cell 8. FIG. 6 shows the embodiment in a sectional view. In contrast to the preceding embodiments, the conductivity meter 1 according to this embodiment now no longer comprises only conductive measuring cells, but also has an inductive second measuring cell 8'.

The first measuring cell 7 has a first conductivity measuring range and is formed by the first electrode 4 and the second electrode 5, wherein the two electrodes 4, 5 are cylindrical in shape and arranged at the housing 3, whereby the first measuring cell 7 is also arranged at the housing 3. The second measuring cell 8' has a second conductivity measuring range and a hollow cylindrical carrier 14, which is also arranged at the housing 3 and on which a transmitting coil 15 and a receiving coil 16 are wound. The cylindrical carrier 14, the first electrode 4 and the second electrode 5 are coaxially arranged one inside the other. Thereby, the medium 2 is, in particular, in contact between the first electrode 4 and the second electrode 5 and with the electrodes 4, 5. Furthermore, the medium 2 is also arranged in the hollow cylindrical carrier 14. The first measuring cell 7 and the second measuring cell 8' are designed in such a way that the first conductivity measuring range and the second conductivity measuring range overlap one another so that a first overlapping conductivity range is formed.

In addition, the conductivity meter 1 has a control device 10 with a change-over switch 11, wherein the control device 10 is designed for controlling the changeover switch 11. In addition, the control device 10 is also designed for controlling the measuring cells 7, 8'. The changeover switch 11 allows for the use of the single control device 10 with the plurality of measuring cells 7, 8'. The changeover switch 11, controlled by the control device 10, connects the control device 10 either with the first measuring cell 7 or the second measuring cell 8', so that the control device 10, during operation, determines a conductivity of the liquid medium 2 at a point in time in each case with one of the measuring cells 7, 8'. Thereby, the connection between the control device 10 and one of the measuring cells 7, 8' is exclusive, which means that the other measuring cell then cannot be controlled by the control device 10. The design of the control device 10 for controlling the measuring cells 7, 8', in particular, comprises the configuration for determining a conductivity of a medium with the measuring cells 7, 8'.

Moreover, the explanations in respect to the first embodiment also apply to the fourth embodiment.

Figure 7:
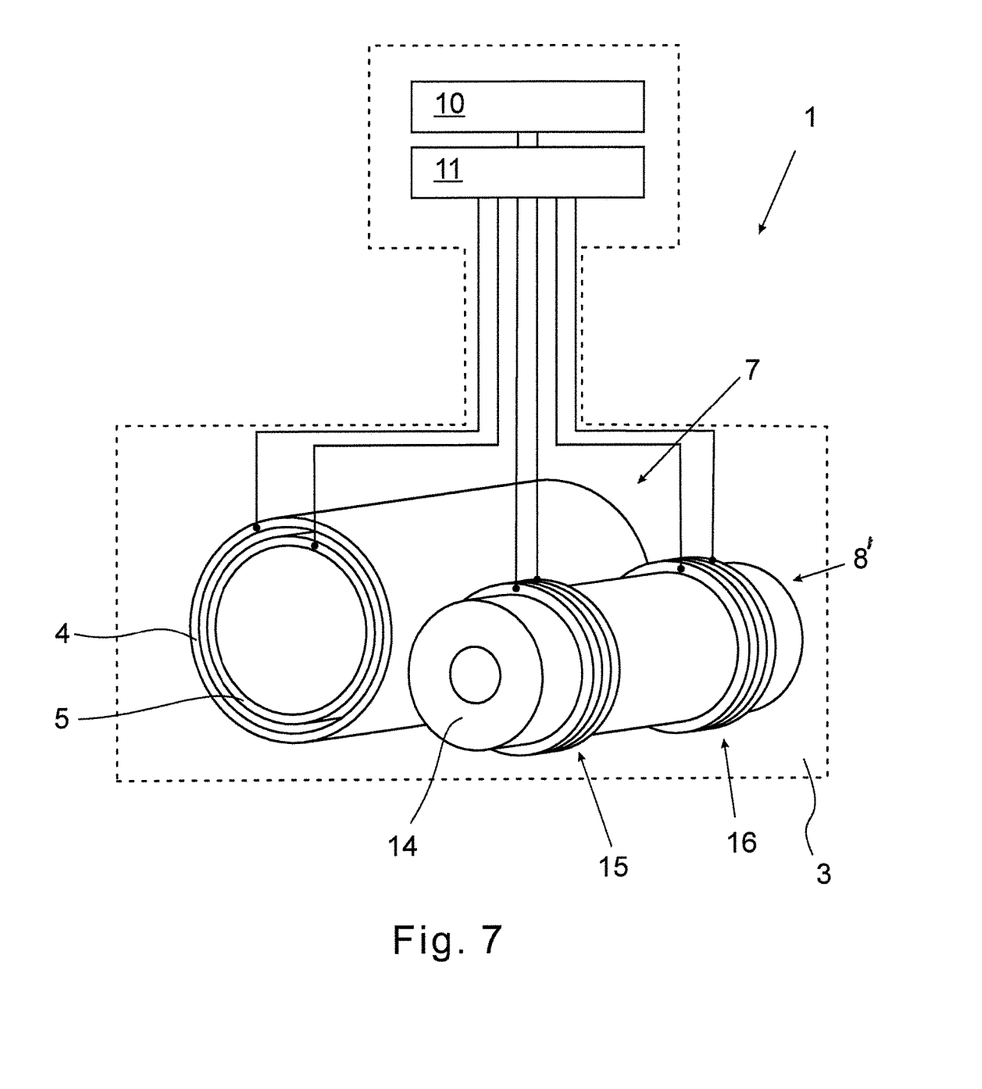
FIG. 7 is a diagrammatic view of a conductivity meter having a conductive first measuring cell and an inductive second measuring cell.

FIG. 7 shows a fifth embodiment of a conductivity meter 1 in an abstracted sectional view. This embodiment corresponds to the fourth embodiment apart from the differences shown in the following, which is why the statements in respect to the fourth embodiment correspondingly apply to the fifth embodiment.

The fifth embodiment of the conductivity meter 1, like the fourth embodiment, has a conductive first measuring cell 7 and an inductive second measuring cell 8'. The measuring cells 7, 8' are, however, not arranged coaxially in one another, but parallel to one another in a plane perpendicular to the support shaft 12. The arrangement parallel to one another is thereby a special form of an arrangement next to one another.

Figure 8:
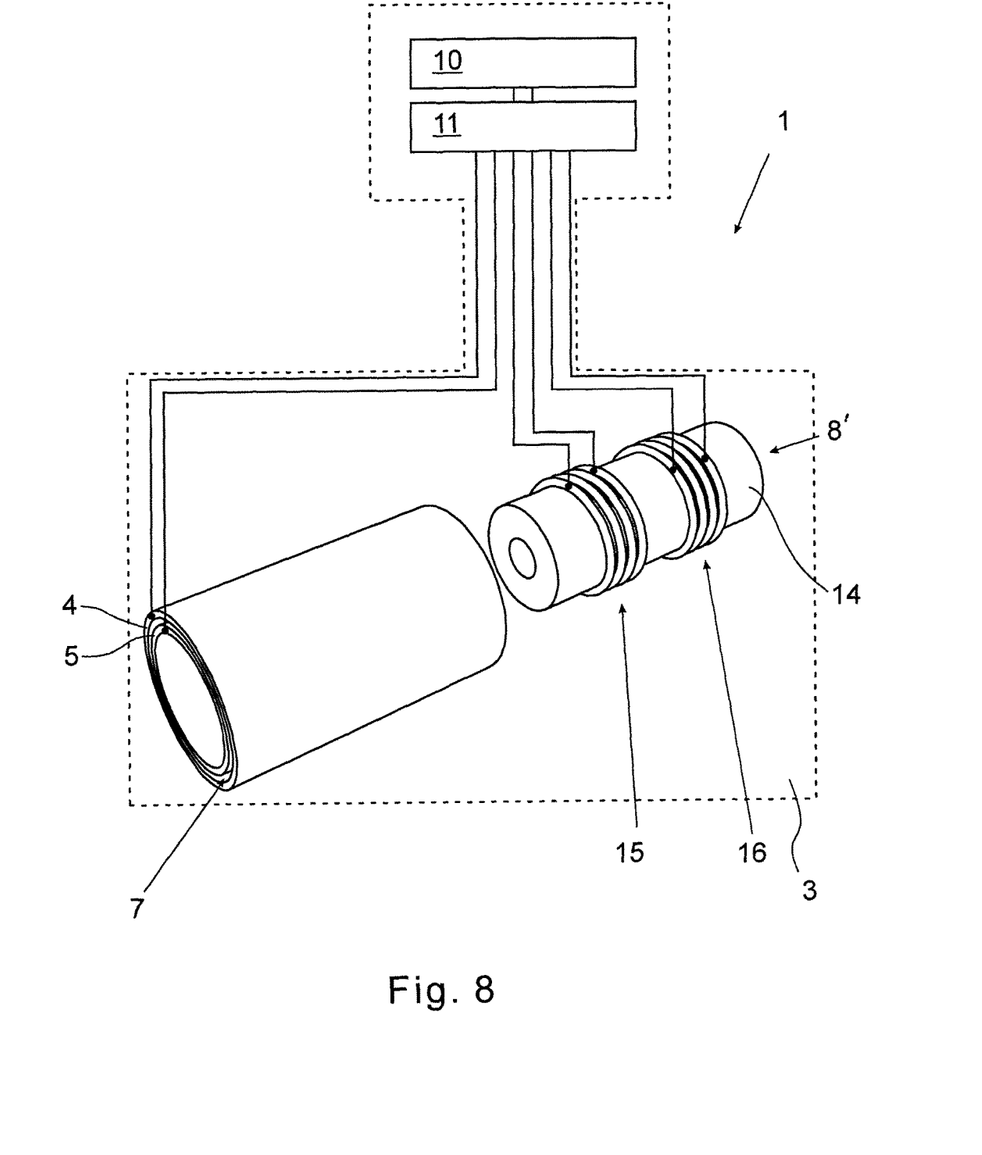
FIG. 8 is a diagrammatic view of a sixth embodiment of a conductivity meter having a first measuring cell and an inductive second measuring cell.

FIG. 8 shows a sixth embodiment of a conductivity meter 1 in an abstracted sectional view. This embodiment corresponds to the fourth embodiment apart from the differences shown below, which is why the explanations for the fourth embodiment correspondingly apply to the sixth embodiment.

The sixth embodiment of the conductivity meter 1, like the fourth embodiment, has a conductive first measuring cell 7 and an inductive second measuring cell 8'. However, the measuring cells 7, 8 are arranged coaxially in series one behind the other, not coaxially in one another. In this embodiment, the first measuring cell 7 is arranged in front of the second measuring cell 8', whereby, in other embodiments, an inverted arrangement is also provided.

Figure 9:
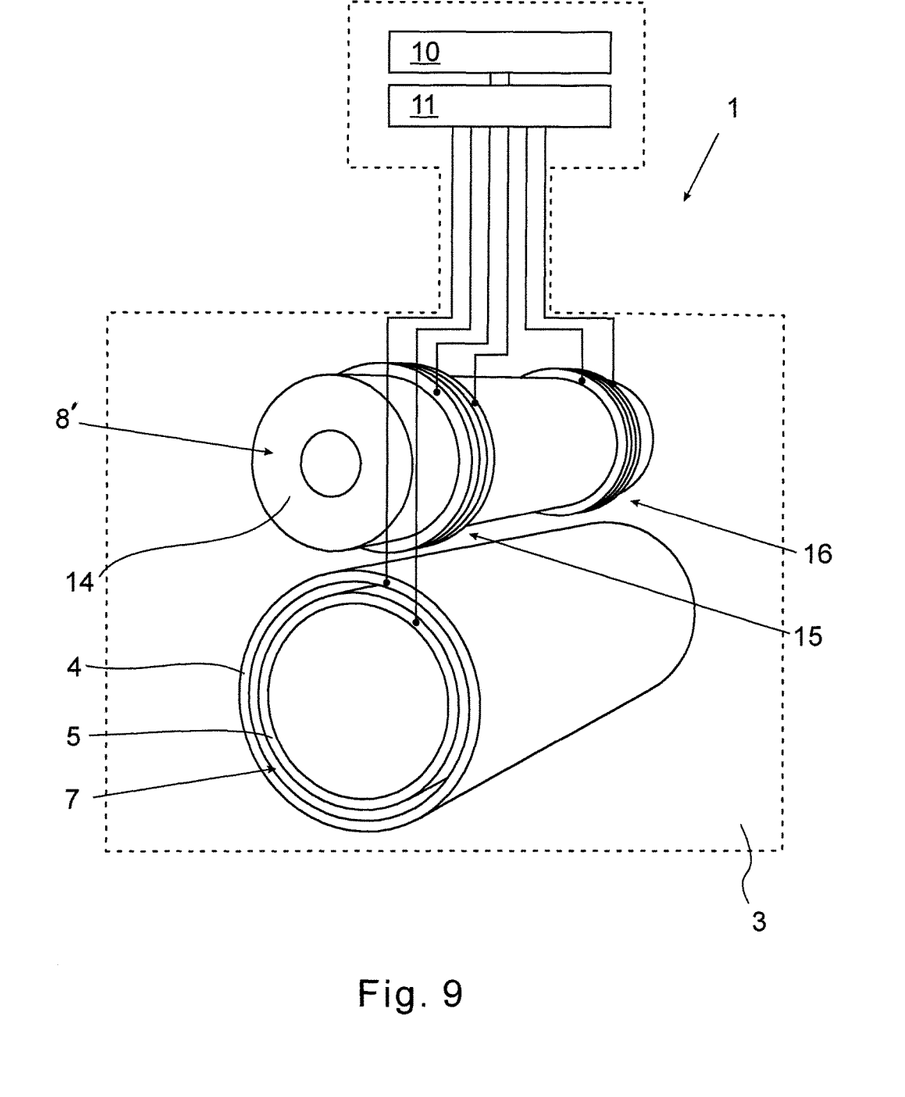
FIG. 9 is a diagrammatic view of a seventh embodiment of a conductivity meter in a sectional view having a conductive first measuring cell and an inductive second measuring cell.

FIG. 9 shows a seventh embodiment of a conductivity meter 1 in an abstracted sectional view. This embodiment corresponds to the fourth embodiment apart from the differences shown in the following, which is why the comments in respect to the fourth embodiment correspondingly apply to the seventh embodiment.

The seventh embodiment of the conductivity meter 1, like the fourth embodiment, has a conductive first measuring cell 7 and an inductive second measuring cell 8'. However, the measuring cells 7, 8 are not arranged coaxially in one another, but the first measuring cell 7 is arranged under the second measuring cell 8 with respect to the support shaft 12.

Figure 10:
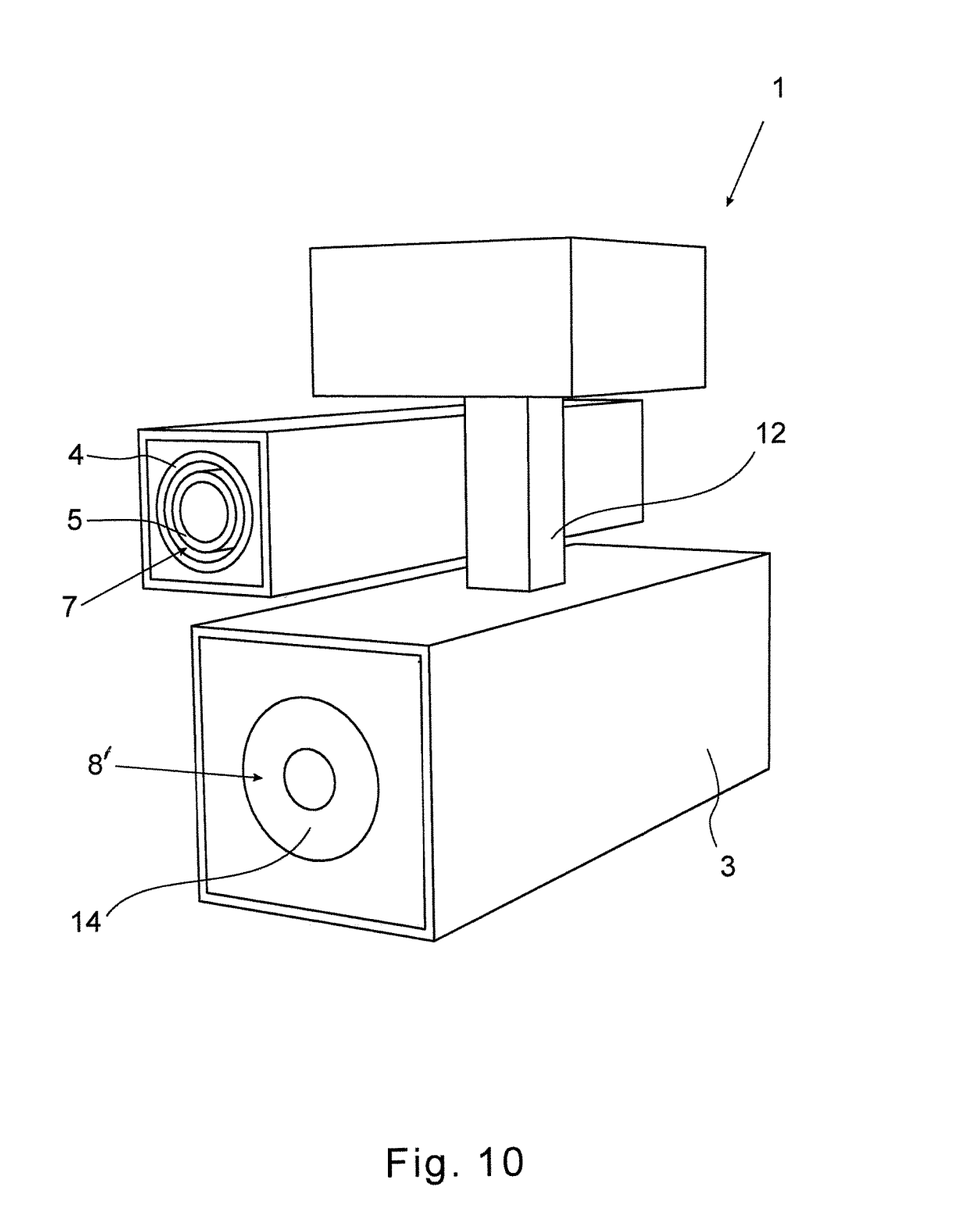
FIG. 10 is a perspective view of an eighth embodiment of a conductivity meter having a conductive first measuring cell and an inductive second measuring cell.

FIG. 10 shows an eighth embodiment of a conductivity meter 1 in an abstracted representation. This embodiment corresponds to the fourth embodiment apart from the differences shown in the following, which is why the statements in respect to the fourth embodiment correspondingly apply to the eighth embodiment.

The eighth embodiment of the conductivity meter 1, like the fourth embodiment, has a conductive first measuring cell 7 and an inductive second measuring cell 8'. However, the measuring cells 7, 8' are not arranged coaxially in one another, but the first measuring cell 7 is arranged on one side of the support shaft 12 and the second measuring cell 8' is arranged at one end of the support shaft 12.

What is claimed is:
1. Conductivity meter for measuring an electrical conductivity of a liquid medium, comprising:
   a housing,
   a conductive first measuring cell having a first conductivity measuring range, a first electrode and a second electrode, and
   a control device for controlling the first measuring cell,
   wherein the first measuring cell and the control device are arranged in the housing,
   wherein the conductivity meter has a second measuring cell with a second conductivity measuring range,
   wherein second measuring cell is arranged in the housing,
   wherein the control device is also controls the second measuring cell, and wherein the first measuring cell and the second measuring cell have conductivity measuring ranges that overlap one another.

2. Conductivity meter according to claim 1, wherein the control device is adapted for determining a first conductivity of the medium with the first measuring cell and a second conductivity of the medium with the second measuring cell, and for signaling an error if at least one of the determined first conductivity and the determined second conductivity lie in an overlapping conductivity measurement range and the determined first conductivity deviates from the determined second conductivity by more than a conductivity tolerance value.

3. Conductivity meter according to claim 1, wherein the second measuring cell is a conductive measuring cell.

4. Conductivity meter according to claim 3, wherein the conductivity meter has a third electrode, and wherein the second electrode and the third electrode form the second measuring cell.

5. Conductivity meter according to claim 4, wherein the first electrode and the third electrode form a third measuring cell with a third conductivity measuring range and wherein the control device is adapted for controlling the third measuring cell.

6. Conductivity meter according to claim 1 wherein at least the first electrode and the second electrode are cylindrical and coaxially arranged one inside the other.

7. Conductivity meter according to claim 1 wherein at least the first electrode and the second electrode are plate-shaped and arranged parallel to one another.

8. Conductivity meter according to claim 1 wherein the conductivity meter has a carrier plate and at least the first electrode and the second electrode are arranged next to one another on the carrier plate.

9. Conductivity meter according to claim 1, wherein the second measuring cell is an inductive measuring cell.

10. Conductivity meter according to claim 9, wherein the conductivity meter has a cylindrical carrier and the inductive measuring cell is arranged around the cylindrical carrier, wherein the first electrode and the second electrode of the first measuring cell are cylindrical and coaxially arranged one inside the other, and wherein the first measuring cell and the second measuring cell are arranged coaxially one inside the other.

11. Conductivity meter according to claim 9, wherein the first measuring cell is one of arranged next to, parallel to, in series with the second measuring cell and under the second measuring cell.

12. Conductivity meter according to claim 9 wherein the housing has a support shaft and the first measuring cell is arranged in or on the support shaft.

13. Conductivity meter according to claim 1, wherein the control device has a changeover switch that connects the control device at least to one of the first measuring cell and the second measuring cell.

* * * * *